(12) United States Patent
Strauss et al.

(10) Patent No.: US 6,566,062 B1
(45) Date of Patent: May 20, 2003

(54) METHOD FOR IDENTIFYING A NUCLEIC ACID

(75) Inventors: Andreas Strauss, Hamburg (DE); Gunther Thumm, Hamburg (DE); Johannes Pohlner, Hamburg (DE); Friedrich Götz, Hamburg (DE)

(73) Assignee: Evotec BioSystems AG, Hamburg (DE)

( * ) Notice: Subject to any disclaimer, the term of this patent is extended or adjusted under 35 U.S.C. 154(b) by 0 days.

(21) Appl. No.: 09/508,524

(22) PCT Filed: Sep. 26, 1998

(86) PCT No.: PCT/EP98/06136

§ 371 (c)(1), (2), (4) Date: May 2, 2000

(87) PCT Pub. No.: WO99/16900

PCT Pub. Date: Apr. 8, 1999

(30) Foreign Application Priority Data

Sep. 27, 1997 (EP) .............................................. 97116841
Oct. 29, 1997 (EP) .............................................. 97118755

(51) Int. Cl.$^7$ ............................ C12Q 1/00; C12Q 1/68; C12Q 1/02
(52) U.S. Cl. .................................. 435/6; 435/4; 435/29
(58) Field of Search .................................. 435/4, 6, 29

(56) References Cited

U.S. PATENT DOCUMENTS 5,616,686 A 4/1997 Fischetti et al.

FOREIGN PATENT DOCUMENTS

| WO | WO96/34976 | 11/1996 |
| WO | WO97/08553 | 3/1997 |

OTHER PUBLICATIONS

Ton–That, H. et al, "Anchor Structure of Staphylococcal Surface Proteins", The Journal of Biological Chemistry, vol. 272, No. 35, Aug. 29, 1997, pp. 22285–22292.
Schneewind, O. et al, "Sorting of Protein A to the Staphylo–coccal Cell Wall", Cell, vol. 70, Jul. 24, 1992, pp. 267–281.
Schneewind, O. et al, "Structure of the Cell Wall Anchor of Surface Proteins in Staphylococcus aureus", Science, vol. 268, Apr. 7, 1995, pp. 103–106.
Samuelson, P. et al, "Cell Surface Display of Recombinant Proteins on Staphylococcus carnosus", Journal of Bacteriology, vol. 177, No. 6, Mar. 1995, pp. 1470–1476.
Rouch, D.A. et al, Trimethoprim resistance transposon Tn4003 from Staphylococcus aureus encodes genes for a dihydrofolate reductase and thymidylate synthetase flanked by three copies of IS257, Molecular Microbiology, vol. 3, No. 2, 1989, pp. 161–175.
Murakami, Y. et al, "Role of the Charged Tail in Localization of a Surface Protein Antigen of Streptococcus mutans", Infect. Immun., vol. 65, No. 4, Apr. 1997, pp. 1531–1523.
Strauss, A. et al, "In vivo immobilzation of enzymatically active polypeptides on the cell surface of Staphylococcus carnosus", Molecular Microbiology, vol. 21, No. 3, 1996, pp. 491–500.

Primary Examiner—Remy Yucel
Assistant Examiner—Konstantina Katcheves
(74) Attorney, Agent, or Firm—Jacobson Holman PLLC

(57) ABSTRACT

A method for identifying a nucleic acid which codes for a polypeptide factor affecting the covalent bonding of polypeptides to the surface of Gram-positive bacteria, comprising the following steps:

a) providing a sample of Gram-positive bacteria which can be genetically altered and contain or produce at least one enzymatic reporter substance which is or can become covalently bonded to the surface of the Gram-positive bacteria, said at least one reporter substance having a different enzymatic activity when not covalently bonded to the surface of the Gram-positive bacteria from that exhibited when it is covalently bonded to the surface of the Gram-positive bacteria;

b) causing genetic alterations in Gram-positive bacteria of the sample;

c) assaying the enzymatic activity of the reporter substance of the Gram-positive bacteria of the sample;

d) separating Gram-positive bacteria which exhibit a different enzymatic activity of the reporter substance from that observed for covalent bonding of the reporter substance to the surface of the Gram-positive bacteria;

e) isolating the nucleic acid of the Gram-positive bacteria separated in step d);

f) identifying at least one segment of the nucleic acid isolated in step e) that carries the genetic alteration;

g) based on the segment identified in step f), identifying a nucleic acid which codes for a polypeptide factor affecting the covalent bonding of polypeptides to the surface of Gram-positive bacteria.

19 Claims, 5 Drawing Sheets

SEQUENCE LISTING

<160> NUMBER OF SEQ ID NOS: 23

<210> SEQ ID NO 1
<211> LENGTH: 604
<212> TYPE: DNA
<213> ORGANISM: Staphylococcus carnosus
<220> FEATURE:
<221> NAME/KEY: modified_base
<222> LOCATION: (1)..(604)
<223> OTHER INFORMATION: "n" represents a, t, c, g, other or unknown

<400> SEQUENCE: 1

| | | | | | | |
|---|---|---|---|---|---|---|
| acccatgttg | gaaagaatca | tattctccat | gtaaatcact | gacaaagtgt | tcagtgcctt | 60 |
| ttgttagatt | ctagactgat | gatttctgta | gcgagttgtt | cttcgtgatt | aaattttcct | 120 |
| gcaagtaagt | caaagtattt | atgtttaagt | tcacgatctg | tggtcttcat | ttcttcctcc | 180 |
| tgtgcttcta | tattaatagc | gcttacattt | gattattgta | cttttttata | aaattttcaa | 240 |
| tggtagcggt | taaattgttg | caaattagtt | gcattaaaag | taaacgattt | caaatttagg | 300 |
| tgagaattag | gtagtattta | ctataatctg | agacaatctc | ctagaaacat | gtgatattat | 360 |
| tatttttgaa | tacaatattt | twacatcagg | aggcattatg | acatccctat | tttctgtaga | 420 |
| gcaattgaac | aaatctttca | aagacagcac | ttttaaaata | aataatgtgt | catttgaagt | 480 |
| gcatgaaggt | gaaattgtag | cgttttttcgg | ccagaacggc | tctggcaaat | ctactttgat | 540 |
| tcgtatgatt | gtgggtgatt | atcccttgtt | ccagggaaat | tgttttttttt | kgtgnngcgg | 600 |
| tggg | | | | | | 604 |

<210> SEQ ID NO 2
<211> LENGTH: 295
<212> TYPE: DNA
<213> ORGANISM: Staphylococcus carnosus

<400> SEQUENCE: 2

| | | | | | | |
|---|---|---|---|---|---|---|
| ctaaaaagga | ggatgccaac | tatgaataaa | tttgacaaag | catatgagat | ttgtgcaaag | 60 |
| agattcttga | aatcggaaat | gaacgtgacg | atcgtacaca | tacaggtaca | atttcaaagt | 120 |
| tcggccacca | attacggttt | gatttatctg | aaggatttcc | attacttact | acaaaaaaag | 180 |
| tttcgtttaa | attattagct | actgaactcg | tttggttcat | aaaaggtgat | actaagatca | 240 |
| agtacttact | tcaatatagt | aataaatacc | ggaatgagtg | ggcatttgaa | aaata | 295 |

<210> SEQ ID NO 3
<211> LENGTH: 429
<212> TYPE: DNA
<213> ORGANISM: Staphylococcus carnosus

<400> SEQUENCE: 3

| | | | | | | |
|---|---|---|---|---|---|---|
| ctattataat | caatattaac | aagccagcaa | gcggaaagca | agcggcttat | tataaattag | 60 |
| caagaggcca | tccaaaaatg | ctaaagcaat | atataccaat | tagttgtcac | ttcttcgtta | 120 |
| ggtattctgc | tactvtctcg | catcaaatgg | tatctttttta | tattctattc | ctgactggtt | 180 |
| tagcagctga | attkcatatt | cacgacttat | gataatcttg | agcataatat | attccttttaa | 240 |
| ttccagcctg | aattattgat | tacgtacaac | ttaaacaagg | aaaatgcgct | acacatatgg | 300 |
| ctgcaccttc | agtagaaaca | ccctgctttt | gtacatcgca | aaaaggcgcg | cacctcagca | 360 |
| cgtactgctc | aacacaacga | ctatcctcca | cgaggcatcc | tctacaatca | cagtgaacca | 420 |
| cctgctacg | | | | | | 429 |

<210> SEQ ID NO 4
<211> LENGTH: 748
<212> TYPE: DNA
<213> ORGANISM: Staphylococcus carnosus
<220> FEATURE:
<221> NAME/KEY: modified_base
<222> LOCATION: (1)..(748)
<223> OTHER INFORMATION: "n" represents a, t, c, g, unknown or other

<400> SEQUENCE: 4

```
kcgggagcct aatactaaaa ataatgaatt caatgtcgaa aattaaactg aatgcattac      60
gtgagcaacg tcatatatta aatgaattgg tagatgaagg agaagtaagt gaaaaaacgg     120
cactgaaagt aagagaagag gttaattatg atgaaatgat tttagtagag tcgcttaact     180
taatatatta aataagctgt aaaacagatg cttagcgacg attgttttgc agctttttta     240
tgtaaaamag gagccagtct tggaggggac tggctctttg aaaagcgata tcatcgatta     300
ccgcttttc cttaggggtt tttgtggtct ctagggagga ttacgagcac tgcttattac      360
ttatgtttag gatagattat ttatgggaga tgacggtatt tgaattagga ggtgaaccgg     420
catcttaagg ataatgtgtt atttcatact gttgtggaca gtttcaatat tagattccmc     480
cattttgtam taggaatcgc ccttactgcc tttttttgcca atagagtctg tataaacttc     540
tccmgaaatc ggtacacctg tttcttcacy taaacyytgc rggacttttg tggggcccca     600
cctggggtyt cgcgccaaaa aggagggttt taagggaagg gattttacaa attgaancgc     660
ctgttcaact tgttcggtgt ccccgttttt ccgaattgag ttccacaata tagcgggtgt     720
aatgccctat ttgtttagag aaatattt                                        748
```

<210> SEQ ID NO 5
<211> LENGTH: 572
<212> TYPE: DNA
<213> ORGANISM: Staphylococcus carnosus

<400> SEQUENCE: 5

```
ggcctataag tatggacagt cacttgttta gagaaatttt tataatttg taaatcaatg       60
actaattttg caacatcttt aggtgccata tataaatttc cagctccata gtattgatct     120
agaaactcag gcttttggaa atcttcata ttattatatc cctgtgccat ataaggttgg      180
aaagttgtgt cgttataaaa agcggttctt tctaaatcat atggcttcgc aaagttatca     240
ttaaaatatt ttgcataaga ttcttttgta acaacttcta ttacgcgtgc caaaacaata     300
taatttccat cattatacat atgcttagtg atacgtacca ggctgaatac cttcattttg     360
catccatttc gatgcgccat ctatgtcatg aatttgactt gtagctttat attttttcaa     420
ccctgttcta tgaagcataa agtcttttaa atagagtggt ttcgctcgtc ttaaaccatg     480
gaagatattt tgtgattgga tcatttatat tcacttttgc ttcagtttct aattttaatc     540
aacatcaggg ccagtcgtaa attttttggg gc                                    572
```

<210> SEQ ID NO 6
<211> LENGTH: 690
<212> TYPE: DNA
<213> ORGANISM: Staphylococcus carnosus

<400> SEQUENCE: 6

```
ctaaaaaaca ataaaadgtg cagtgtagaa aattaattct agcgactgac tttttatta      60
tgatgctta tcattgaaaa ttgcattaag gttaaagaat ttagttaatg catttccgct     120
```

-continued

| | |
|---|---|
| ttgttgatta ttattgcctt ggtattatta ccttgttgat tattattgcc ttggagttat | 180 |
| taccttgttg attgctttgt ccagaactat tatttgaacc actgttacta ctgctgctgc | 240 |
| caccatttac agtaccgtta ctattaactt ttctattagt agtatcgttg tctgggtgtc | 300 |
| cagctacaga taaatcttct ttgcttgaac catctacaga agaaggtttt ttgaagtctg | 360 |
| caccgtcacg aggactaatg tctgacatta caatcttcaa gtaaatattg tggataatct | 420 |
| tgttcactat gaccaaacaa atgaattttc accataattg tttttactta ttgaaagcca | 480 |
| tccaaaactg acattgaata tttaggtgtg aaacaattaa tccaacatct ttggctgccg | 540 |
| tcatcggtaa gttgtattgt tgaaaatgtt tcactaccgt aagtaacctg tcccagtttt | 600 |
| tgctgctaga ttaacaacct gaaacgccgt gtcccaaaaa agcagaaccc caagcttcaa | 660 |
| aagtaccttt taaagaaatt cctgaaaggc | 690 |

<210> SEQ ID NO 7
<211> LENGTH: 459
<212> TYPE: DNA
<213> ORGANISM: Staphylococcus carnosus

<400> SEQUENCE: 7

| | |
|---|---|
| cataataagg tcgatactca gggttttgta ttaactcttt ttgtgaatgt cctcaaattt | 60 |
| tcctagtgaa cgttctctta acaatgctgt aatagtaaca ggaatagtgt tatcaaaacc | 120 |
| attttcatag gtctgtacag tcctctttaa atctgaaaca taaatatggt caataggaat | 180 |
| atctgaaaag tattctttca attttttttgc tgacttgata cctgtttcag tcaaagcaac | 240 |
| atttagttga ccgcaaaagt aatcttgccc gtgtttatta tcataatttg ctgtcgattc | 300 |
| tccgtctcga attaaataaa tctccaagtt gtctcactcc aattattaac ttactttcag | 360 |
| gccagttact ttactgatat ctttatwwag ataataaagt tatagacacc actaaatatt | 420 |
| ttattcaaca gtatgataac acggttttwa tcaatatat | 459 |

<210> SEQ ID NO 8
<211> LENGTH: 800
<212> TYPE: DNA
<213> ORGANISM: Staphylococcus carnosus
<220> FEATURE:
<221> NAME/KEY: modified_base
<222> LOCATION: (1)..(800)
<223> OTHER INFORMATION: "n" represents a, t, c, g, unknown or other

<400> SEQUENCE: 8

| | |
|---|---|
| ccagattaga agtatatacc agaagaagct gagaagcacc tggtactctt gttgggtatg | 60 |
| ccgataatta catgaaagtt gaatttgaag gtgacgattc attaatagga gagttggttc | 120 |
| gtgttaaaat tacacaagct ggatatccat tgaatcaagg acatgtagtt mkagttattg | 180 |
| accatgcatc taaccgtagt gaatttactg ctattattta agattcaaaa aattaattat | 240 |
| tctaattgac cccaactatc atatatatta tacttatgaa tgcgtcatat ttagttatgc | 300 |
| tatgtatatg aaaataaagt tccgttgata tttggaggga gggaaataca gatgtctaaa | 360 |
| acmgtagtcc gtaaaaacga atcacttgaa gatgctttac gccgtttcaa acgctcagtt | 420 |
| tcaaaaagcg gtacaattca agaagtacgt aaacgtgaat tttacgaaaa accaagtgtt | 480 |
| aaacgtaaaa agaaatcaga agctgcacgt aaacgtaaat ttaaataatt gatatgtctg | 540 |
| ttgactccct caacaacaaa tatgaattat ataaatgccg ttttcgaag gtcatatata | 600 |
| ttaccaattc aggtagtatt tatggccttt tttcttctca ttttaaaatc aaatatatt | 660 |
| ttctataaat tcactctttt ataactataa ttcctttaag tagtcmtgta taatgaaatg | 720 |

```
agagcgaggt gaattttttgt ctcatcccac ctgggggattt ttacctaata atttccgtgt    780
ttcagactag tcnaagcccc                                                 800

<210> SEQ ID NO 9
<211> LENGTH: 684
<212> TYPE: DNA
<213> ORGANISM: Staphylococcus carnosus
<220> FEATURE:
<221> NAME/KEY: modified_base
<222> LOCATION: (1)..(684)
<223> OTHER INFORMATION: "n" represents a, t, c, g, unknown or other

<400> SEQUENCE: 9
ctattagtaa aaacaacaga aagatagatt gtattagtaa aaacaacaga aagatagaga      60
tatggagcaa ttattttttct tttccttatt ttagtttaca taatatatat tataggaagt   120
tatatataga acgagagaga gtgctttgca tatccctatt tatatgtgta tgtcttattt    180
tgtattgttg ttcagcttttt atttaactac atattagcga actctatttc ttgttactca   240
tgtgtttgta attacatagc catgaggttt acgtttcgac tatatcgata tggaatcgca    300
actataatgg tatataacga tatatgtaaa tcagttataa acgacatgt ataaggtacg     360 tatataaagt tatatgaata actcagttaa tgatatagat gctataagtg tatgtgtctt    420
aaaacttcat ttagtttaca taatctaaaa tacactatta aaaacacacc agattctcat    480
atatccggtg tgttttgcagt attattcttg ataaacatct attaaggcgt tgggataatc   540
atcacggtct gcactaaata tatctttttgt tttgaaatca tccacaattg taccattatt   600
taacacaaat catacgganca acaattttgat ttaaagtact gcaaatatca tgcgagggg  660 tatcatcgta gttgctggtc ttta                                         684

<210> SEQ ID NO 10
<211> LENGTH: 915
<212> TYPE: DNA
<213> ORGANISM: Staphylococcus carnosus

<400> SEQUENCE: 10
cccttatagc aaaaggagct tgaaactttg tcatgctttt actacttgtt tccattgttc     60
atatcactca agtttccaaa tcctctgcaa atacgcgtaa tctttttatt ggatttcgca   120
gccatcgcac ctatcaaaat atcagctgga atgacattca acactactac caatcacttg    180
aattaaaata cttcaagcgt ctttttatata tcagcatttt gttcgcattg atagacatca   240
ttacgttgct gaagtaccat actgcttggt taatccttgc agaattatgt atttacttca    300
ttacacttat ttttgttatcc aaaaaagtag aacattatat cgcacaaaaa ggaaagtagt  360
tgtaatccta tcgaaagagg gagagttcgt tccaaagtag gatggcagca ggtatttaat   420
ccgctataat ttaagttatt aaattagaaa gtcaggtttt taatatgtca gcaatccaca   480 gaaatatat tgcctctact ttaattatct taatagcttt aatggtgctc gtgaaatcga   540
acctgattct tttcatagat gagccggtat atcgcttagt gagattgctt cgcatatccc    600
atttgccaat accttcttgt cctattactc agatattttt tcaccttggc atatggttgg   660
tgtaaaggtt gttatttaac gaatctctta ttcaaaaatc gtcgtctcgc ttatattaca   720
actatttggg caacttccac attattgctc ggcatttggt ctgaaatatt ttatccaccg    780
tccaagaccc agtagattat atttcaggtt ataggttccc cagcttggca taccattggg   840
ccaatagccg gagcggcggt gccttttaaa tgcgggtccg gacgatttta ttggcataat   900
```

```
cctggttatt aacgg                                                          915

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Motif
<221> NAME/KEY: MOD_RES
<222> LOCATION: (3)
<223> OTHER INFORMATION: any, other or unknown amino acid

<400> SEQUENCE: 11

Leu Pro Xaa Thr Gly
 1               5

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ataaggcgcc ttagtttaat tatgctttgt gattc                                     35

<210> SEQ ID NO 13
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgcaggaagc ttaccacaat ctaagaaatc tgaaatatct caagcaagtg gagaag             56

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aataaggcgc ctcattatcc acctgtttca ggtagttc                                 38

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
acgaaagctt accacaatct aagaaatctg aac                                      33

<210> SEQ ID NO 16
<211> LENGTH: 3539
<212> TYPE: DNA
<213> ORGANISM: Staphylococcus carnosus
<220> FEATURE:
<221> NAME/KEY: modified_base
<222> LOCATION: (1)..(3539)
<223> OTHER INFORMATION: "n" represents a, t, c, g, unknown or other
```

<400> SEQUENCE: 16

```
atcacgttat caagtttatc aatagaatca acttcctgtg cttttggaa taaaatctta      60
attaattcca tttgacgttg tccacgtttt aagtctgaat catgatgtct agttctagca     120
aactgctaaa gcctcatcac catttaattt ttggtaccct attttaattt taatcttacc     180
agtatcatct gtgttaggtt catttaagtc gtatggcaca tcatagtata tgccaccaag     240
ctcatttaca gcctcgacaa atgctttcat attgactctc acataataat caacaggtac     300
attcatggta gcttctaccg aatccattgc ggcaattgga ccaccatatg catgtgcatg     360
ggtaatctta tcgtaatagc caactttagg aatgtagctg atagtatcac gtggaatact     420
aagcattcta atttgatgtt ttgattgatt aaaagtagtt aaaatcatag cgtctgatct     480
agagtgttca gcatcctgtc cttttttct tcttccatcg ttatcatcga tacctaagaa     540
aagaatagag ataggttgtt cttcgggatt gactttatta tctcttaagt tggattgacg     600
attagcattt tgctgtcta gagaagattc gaatgcatct tgggacgttt taaaagtaa     660
cgtagcgaag actattggaa caacaatgag aaccaatgct agaaggatca aaagtatt     720
taaaaattta ttcatgattg atgctcctat attaaatttt tgttaaatca taatcataat     780
tttaaaatat aattagttga acgatatta tacaacttca ttactaatac attatagcct     840
taaattgtag tactttatag taaaaaatac aaatgttatg tcaaagttcc ttgtaattg     900
aatgttttgt taaaatcaaa aagcatttt aaaaatataa tgcgactta gtatgatgtc     960
ttaaaaaatt taaaggcgta atataaaatc gagtgattta tacaaagtga taaggtataa   1020
ttaattttgt tgtatagata acatattaga aaaacttatt actatgtagc gtaaagcata   1080
aatgaatgat aagttaattt ttgtaagttg tattattagg catctaggtt caaatttta   1140
acgatctaaa gacataaaat gaatacattg tgaggcaatt atcaaatgaa atttaataaa   1200
nnnnttttg tgtactatta tttatcatta tttctatagc gttaatttt catcgattac   1260
agacgaagac acattctata gacccaatac ataaggaaac aaaattatca gacaatgaaa   1320
aatatttagt ggatcgtaat aaggaaaagg ttgcgccgtc taaactaaaa gaggtatata   1380
atagcaagga tcctaaatat aagaaaattg acaagtattt acaaagttca ttatttaacg   1440
gttcagtagc tatatatgaa aatggcaaat tgaaaatgag taaaggttat ggatatcaag   1500
attttgaaaa aggtattaaa aacacaccga atacgatgtt tttaataggt tcagctcaaa   1560
aattttcaac agggttactg ttaaaacagt tagaagaaga acataaaata aatatcaatg   1620
atccagtaag taaataccttt ccatggttta aacatctaa gcctatccca ttgaaagatt   1680
taatgttgca tcaaagtgga ttatataaat ataaatcctc aaaagattat aaaaatttag   1740
atcaagcagt taaagcgatt caaaacgtg gtattgatcc taagaaatac aaaaagcata   1800
tgtataacga tgggaattat ttagtacttg cgaaagtaat tgaagaagtt acaggtaaat   1860
cttatgctga gaattattat acaaaaatag gagatccttt aaaacttcag cacacagcat   1920
tttatgatga acaaccttt aaaaaatatc tagcaaaagg ttatgcttat aatagtacag   1980
gactttcatt cttaagacct aatatttgg accaatacta tggtgcaggt aatttatata   2040
tgacaccaac agatatgggt aaattaatta ctcaaataca acaatataaa ttattcagtc   2100
ctaaaataac caatccatta ttacatgagt ttggtacgaa acagtatcca gatgaatatc   2160
gatatggttt ctatgctaag ccaacattga atagacttaa cggggattc tttgacaag   2220
tcttttactgt ttactataat gataagtatg tagttgtact tgcattaaat gtaaaaggaa   2280
```

-continued

| | |
|---|---|
| acaatgaagt tcgaatcaaa catatttata atgatatttt aaaacaaaat aaaccttaca | 2340 |
| atacgaaggg tgttattgtt caataattaa tatagaagat ataacatgta tatggcatta | 2400 |
| aggcatcgac cttatctgac cagtatacga gttatatctt ctttttttata gtggtaaaaa | 2460 |
| gtttaaagta taaggttgaa gaaggatgag tttaaaaata tgtgttaact gataaaaggg | 2520 |
| gaaatcattt ggtgagttgg catcagacta aaatgaatga agacgaatac cttggtccat | 2580 |
| gcgtggtgtg aatgttttct aaatctaact ggaaatgata atttaataat gtacactttt | 2640 |
| gattgtttaa acatgtacaa ttttttaaaaa cctaggggata attttattga cgtgaacaac | 2700 |
| attgagatta tctttagaca taaatatgga ttttgaagtt actatattta ttagttgtgg | 2760 |
| gtgttaatgt attaattgaa ttgattataa tgattgtctt ataagatata aaggggact | 2820 |
| taaccattta aaaattgaag ggaaataaaa accagctaac aaaagtgtta gctggttaaa | 2880 |
| ctttacatta ttaaaatgtt gtttataagt gtgaagagtg accgccttgc ataacccaat | 2940 |
| atgttccgac aacgaaacaa agtgtaatta caagagcaaa gataactttg aatgttttgta | 3000 |
| aagcgtccat ctttaccttc agttaaatgc atgaacatta ataattgaag tcgctgcttg | 3060 |
| gacgaatgca aagccaaaga taattgtcaa cttcgcgtgg aatgttaatg acggtgtata | 3120 |
| gtgttacgta aactgctaaa agcgttaata cgatagatgc gataaatcct acagtatgtt | 3180 |
| tcattattgt actcatccgc tatacatcca tccctatcat atatacggca gtaaagatga | 3240 |
| aaacccaaag cgaacatcta agaagtgcca gtataaactt actataaata attttggcgc | 3300 |
| attatatttg tctaatccgc gtcgttggat ttggatgtaa taaacaatat ggcccaagac | 3360 |
| gatacctagc gatacgtgac aaccatgcgt tcctaatagg ataaagaaac tagaccgagt | 3420 |
| aagaaccaat tgttgggtta acgcgcttct gatgcgatag tgtgcgaatt cgataaattt | 3480 |
| cgaatgccaa caaagactaa acctaaaagt aacgtaatga tcatccaaaa catcattaa | 3539 |

<210> SEQ ID NO 17
<211> LENGTH: 1474
<212> TYPE: DNA
<213> ORGANISM: Staphylococcus carnosus
<220> FEATURE:
<221> NAME/KEY: modified_base
<222> LOCATION: (1)..(1474)
<223> OTHER INFORMATION: "n" represents a, t, c, g, unknown or other

<400> SEQUENCE: 17

| | |
|---|---|
| tagatgaaag tgaggaccgc gtatgacgga aaacaaagga tcttctcagc ctaagaaaaa | 60 |
| cggtaataat ggtgccaaat ccaactcaaa aaagaataga aatgtgaaga gaacgattat | 120 |
| taagattatt ggcttcatga ttattgcatt ttttgttgtt cttttactag gtatcttatt | 180 |
| gtttgcttat tatgcttgga agcacctgc atttaccgaa gctaaattac aagatccgat | 240 |
| nnnnnnaaag atatatgaca agaacggaga acttgtaaaa acattagata atggccaaag | 300 |
| acatgagcat gtaaatttaa aagacgtgnn gaaatcaatg aaagacgcag tacttgcaac | 360 |
| tgaagacaat cgtttctacg aacatggcgc acttgattat aaacgtttat tcggtgcaat | 420 |
| tggtaagaac ttgactggtg gatttggttc tgaaggtgcc tcaacattaa cacaacaagt | 480 |
| tgttaaagat gcattttttan caaaacataa atctattgga cgtaaagctc aagaagcata | 540 |
| cttatcatat cgtttagaac aagagtatag taagatgat atcttccaag tatatctaaa | 600 |
| caaaatttac tattctgatg gcgtaannnn nnnnnnnnn nnnnnnnnn nnnnnnnnn | 660 |
| taacgatgca cctaagaaat tcgctgccaa acttggctta aactacgaag gcgatattgg | 720 |
| tccatctgaa gtacttggtg gttctgcttc agaattctca caaacacaat tagcatcagc | 780 |

```
atttgctgca atcgctaacg gtggtactta taacaacgcg cattcaattc aaaaagtagt    840
tactcgtgac nntgaaacaa tcgaatacga tcatactagc cataaagcga tgagtgatta    900
cactgcatac atgttagctg agatgctaaa aggtacattt aaaccatatg gttctgcata    960
tggccatggt gtagctggag taaatattgg tgctaagaca ggtactggta cttacggtgc   1020
tgaaacttat tcacaatata atttacctga taatgcagcg aaagcagtgt ggattaacgg   1080
ctttacacct caatacacta tgtcagtgtg gatgggcttc agtaaagtta acaatatgg    1140 tgaaaactca tttgtgggac atagccaaca agaatatcca cagttcttat atgaaaatgt   1200
gatgtcaaaa atttcatcta gacatggcga agactttaaa cgtcctagct cantaagtgg   1260
tagtatccca tncaatcaat gtttctggta gtcaagataa caacactaca aatcgtagta   1320
cacacggtgg tagtgacaca tcagaaacag cagtggtact gcacaatcaa ataacaatac   1380
tagatctcaa caatctagaa acagcggtgg attaacaggt atattcaact aatccacaca   1440
acataaaatc ctcagttata ccatatttat ggcg                               1474
```

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Motif

<400> SEQUENCE: 18

Leu Pro Ser Thr Gly Glu
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Motif

<400> SEQUENCE: 19

Lys Arg Lys Glu Glu Asn
 1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Motif

<400> SEQUENCE: 20

Ile Ser Gln Ala Ser
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Motif

<400> SEQUENCE: 21

Leu Pro Glu Thr Gly Gly
 1               5

<210> SEQ ID NO 22

```
-continued

<211> LENGTH: 6
<212> TYPE: PRT
<213> ORGANISM: Artificial Sequence
<220> FEATURE:
<223> OTHER INFORMATION: Description of Artificial Sequence: Motif

<400> SEQUENCE: 22

Gly Gly Gly Gly Gly Lys
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Motif

<400> SEQUENCE: 23

Lys Gly Gly Gly Gly Gly
 1               5
```

METHOD FOR IDENTIFYING A NUCLEIC ACID

The present invention relates to a method for identifying a nucleic acid which codes for a polypeptide factor affecting the covalent bonding of polypeptides to the surface of Gram-positive bacteria, and to the nucleic acids obtainable by said method.

In view of the increased occurrence of antibiotic-resistant strains, infections in humans caused by Gram-positive bacteria are an increasing therapeutic challenge. The pathogenesis of these organisms is associated with a wide variety of bacterial surface proteins. Thus, pathogenicity factors anchored to the cell wall are known which promote bacterial adhesion by the binding to extracellular matrix components of the host tissues, such as collagen. Other factors bind serum components, such as IgG, and thus conceal the authentic bacterial surface from the host's immune system. Therefore, selective inhibition of the binding reaction of these proteins to the bacterial cell wall is of great medical interest.

Schneewind et al. (Cell, Vol. 70, p. 267–281, 1992) have studied the anchoring mechanism of protein A in the cell wall of Staphylococci. Protein A belongs to a growing class of surface proteins of Gram-positive bacteria which are characterized by a succession of the characteristic sequence motif LPXTG, followed by a group of 15–22 hydrophobic amino acids, and a C-terminal group of 5–12 charged amino acids. The conservation of these elements is considered an indication of a common export mechanism of these proteins in different Gram-positive species. In order to establish the localization of protein A (discrimination between protein A anchored in the cell wall and secreted protein A) in *S. aureus*, the authors employ radioactive labeling methods. The importance of the above mentioned sequence elements to cell wall anchoring is supported by using hybrid proteins and through mutagenesis of the LPXTG motif and of the C terminus. However, Schneewind et al. are concerned neither with enzymes which might catalyze the anchoring of the surface proteins, nor with their inhibition.

The cell wall anchoring elements in surface proteins of Gram-positive bacteria are also the subject of another article by Schneewind et al. (EMBO J., Vol. 12, p. 4803–4811, 1993). It is shown that enterotoxin B, a protein normally secreted into the medium, can be anchored in the Staphylococcus cell wall through C-terminal fusion to the protein A anchoring signal. The results support the hypothesis that the cell wall sorting is accompanied by a proteolytic cleavage of the polypeptide chain at the C terminus. Presumably, the LPXTG motif is the site of such cleavage and covalent binding to the cell wall while the charged sequence segment serves as a retention signal during the cell wall sorting. The relevance of the geometrical length of the hydrophobic domain, which is dependent on the folding properties, is confirmed by experiments.

An article by Samuelson et al. (J. Bacteriol., Vol. 177, No. 6, p. 1470–1476, 1995) is concerned with the cellular surface display of recombinant proteins on *Staphylococcus carnosus*. The surface display of the malaria peptide M3 is effected using the promoter, secretion signal and propeptide region of the lipase gene of *S. hyicus* and the cell wall anchoring regions of protein A of *S. aureus*. The hybrid protein structure further includes a serum albumin binding protein which serves for the detection of the recombinant surface-anchored proteins in a colorimetric sandwich assay. Further detection methods comprise immunogold electron microscopy, immunofluorescence assays and fluorescence-activated cell sorting (FACS). Samuelson et al. are not concerned with the exact molecular mechanisms of cell wall anchoring either.

The structure of the cell wall anchor of the surface proteins in *Staphylococcus aureus* is the subject of a report by Schneewind et al. (Science, Vol. 268, p. 103–106, 1995). The authors use a combination of molecular-biological and mass-spectrometric techniques and are able to show that after cleavage of the surface protein between threonine and glycine of the conserved LPXTG motif, the carboxy group of threonine is covalently bonded via transpeptidization to the murein sacculus with the free amino group of the cell wall pentaglycine. However, Schneewind et al. also fail to identify or characterize the protein believed to be responsible for proteolysis and transpeptidization, the so-called sortase.

Strauβ and Götz (Molecular Microbiology, Vol. 21, p. 491–500, 1996) are concerned with the in vivo immobilization of enzymatically active polypeptides on the cellular surface of *Staphylococcus carnosus*. They have constructed a hybrid protein which consists of *Staphylococcus hyicus* lipase and the C-terminal region of *Staphylococcus aureus* fibronectin binding protein B (FnBPB). To study the cell wall association of the prolipase, or the proLipFnBPB hybrid, the authors use a prolipase-specific antiserum in an immunofluorescence assay and immunoblotting. Further examinations have demonstrated that a distance of about 90 amino acids between the C terminus of the enzyme and the cell wall sorting signal is evidently indispensable to an efficient folding of the lipase into its active conformation. The influence of greater distances has been examined on fusions of proLip and the C-terminal region of *S. aureus* protein A (proLipSPA, spacer with 165 amino acids) and *S. aureus* fibronectin binding protein A (proLipFnBPA, spacer with 223 amino acids). Additional experiments were performed with *E. coli* β-lactamase as the reporter molecule.

International Patent Application PCT/US 96/14154 (International Publication No. WO 97/08553) describes a method for the stable non-covalent display of proteins, peptides and other substances on the surface of Gram-positive bacteria. Comparative studies between the non-covalent display process and the covalent display process, which has been described in more detail above, were performed. When the C-terminal sorting signal of protein A, which results in covalent display, was replaced by the cell wall targeting signal of lysostaphin ($SPA_{CWT}$), an essentially unchanged binding intensity of FITC-labeled IgG to the Staphylococcus surface could be observed.

U.S. Pat. No. 5,616,686 discloses a polypeptide consisting of about 6 to 20 amino acids which contains as an integral part a peptide construct which is responsible for the anchoring of virulence-determining proteins on the surface of Gram-positive bacteria. In particular, this construct is characterized by containing the amino acids L, P, T and G at positions 1, 2, 4 and 5, respectively, of the amino acid sequence. Due to the homology of these peptides with the sequences of the virulence determinants in the wild type surface proteins, the former presumably react with enzymes involved in anchoring. The result is that the virulence determinants of the bacteria cannot be anchored or can be anchored only to a lesser extent, and thus the progress of the infection is prevented. However, the enzyme or enzymes involved in surface anchoring are not characterized in this patent specification either.

International Patent Application PCT/US 93/02355 (International Publication No. WO 93/18163) is concerned with the provision of fusion proteins which contain at least the anchoring region of Gram-positive surface proteins as well as varying proteins, polypeptides or peptides, especially those having a therapeutic effect in humans and animals. The anchoring region comprises an LPSTGE segment, a spacer segment of the sequence TAN, a hydrophobic segment consisting of 20 amino acids, and a charged segment with the sequence KRKEEN.

Therefore, it is desirable to provide a method which allows the identification of nucleic acids in Gram-positive bacteria which code for those polypeptide factors which directly or indirectly affect the covalent bonding of polypeptides to the surface of the Gram-positive bacteria.

Surprisingly, this object is achieved by the method of the present invention.

"Polypeptides" within the meaning of the invention means polymers usually composed of at least 20 amino acids and also comprises proteins, in particular. The amino acids are represented by the one-letter code where X represents an arbitrary amino acid.

In the following, the basis of a preferred embodiment of the method according to the invention shall first be set forth before the method for the identification of nucleic acids is dealt with in detail.

In a preferred embodiment, the method according to the invention is to be considered an enzymatic reporter assay which detects the effect of mutations on bacterial factors (targets) which directly or indirectly participate in the LPXTG-motif-dependent C-terminal anchoring of polypeptides to the surface of Gram-positive bacteria. Among the large number of factors and processes which may have an effect on this process, the present invention preferably aims at those enzymatic steps which take place after the beginning of the translocation of the cellular surface polypeptides over the cytoplasmic membrane. In addition, the method according to the invention in part covers enzymatic and other targets which participate in the biosynthesis of cell wall murein. From the phenotypic characteristics of the cells used in the respective method, mutations can be assigned to particular groups of targets.

In a particularly preferred embodiment of the method according to the invention, the cellular and molecular basis of the reporter assay is a recombinant *Staphylococcus carnosus* clone which contains a selectable expression plasmid with an inducible reporter gene fusion. The gene fusion codes for a hybrid polypeptide consisting of an N-terminal signal peptide, a precursor protein of *Staphylococcus hyicus* lipase and a C-terminal portion of the fibronectin binding protein B (FnBPB) from *Staphylococcus aureus*. After being produced in the cytoplasm, the hybrid polypeptide is transported through the bacterial cell membrane due to its N-terminal signal structures, and processed at the amino terminus by a signal peptidase. Further, a cleavage in the C-terminal LPXTG recognition motif is performed, and the remaining hybrid protein is covalently linked to the murein. It has been experimentally established that different lengths of the FnBPB portion influence the building of enzymatic activity of the lipase fusions differently. One construct was identified which exhibited no lipase activity in its cellular-surface bound form (coded by plasmid pTX30Δ82). However, if the corresponding fusion was released from the bacterial surface by treatment with lysostaphin after having been covalently anchored, the full lipase activity was achieved. Within the scope of the present invention, it has been recognized for the first time that interferences with the cell wall anchoring of the lipase function result in a release of the fusion with a concomitant occurrence of lipase activity in the culture supernatants in the assay clone in question. As possible targets, various cellular factors may be considered which can be essentially divided into two groups according to their growth behavior.

One target or group of targets is the enzyme or enzyme complex designated as sortase which effects the carboxy-terminal cleavage of relevant polypeptides in the LPXTG motif and their subsequent covalent bonding to peptide components of the cell wall murein, such as interpeptide bridges, especially pentaglycine units, on the surface of the bacteria. Although the inhibition of these functions presumably leads to the release of surface-bound factors and thus presumably to the attenuation of pathogenic bacteria, it probably does not lead to significant impairments of the viability and dividability of the bacteria. A characteristic phenotypic feature of this group of targets in the assay procedure is the release of lipase activity into the assay medium while the growth behavior of the bacteria is more or less unaffected. In contrast, the impairment of a target or group of targets having an essential function in murein synthesis results in massive changes in the viability and dividability of the bacteria which are phenotypically detectable.

To demonstrate the potential suitability of the method according to the invention for the examination of the target "sortase", two different inhibition/mutation scenarios have been simulated using hybrid proteins which have been genetically engineered in a well-aimed manner (see Example 1 and FIGS. 1 and 2).

After induction of the xylose promoter, *S. carnosus*/pTX30Δ82.mem produces a hybrid protein consisting of *S. hyicus* prolipase and the C-terminal fragment of *S. aureus* fibronectin binding protein B (FnBPB) wherein the LPXTG motif, which is important to the anchoring to the cell wall, has been exchanged for the sequence ISQAS (FIG. 1). In other embodiments, however, it may also be exchanged for any other sequence which preferably consists of 5 amino acids. In a further embodiment, LPXTG substitution is not necessary for the mem phenotype, but a complete deletion of the LPXTG motif may also be considered. Thus, the specific cleavage at the LPXTG motif and hence the covalent binding to the murein sacculus do not take place. Surprisingly, it could be shown that the hydrophobic anchoring sequence which is thus retained at the carboxy terminus of the fusion is evidently not sufficient to anchor the lipase stably and especially in an inactive form in the cell coat and thus at the cellular surface. The lipase activity is quantitatively released from the bacterial surface into the culture medium. Thus, this clone simulates the inhibition of the cleavage reaction by sortase, an essential step which precedes the covalent bonding of the N-terminal cleavage product to the murein at the cell wall.

After induction of the xylose promoter, *S. carnosus*/pTX30Δ82.sec produces a hybrid protein consisting of *S. hyicus* prolipase and a C-terminal fragment of *S. aureus* fibronectin binding protein B (FnBPB) which ends with the motif LPETGG (FIG. 1). This clone simulates the inhibition of the (covalent) bonding reaction between the lipase hybrid protein to be anchored, which has already been processed at the C terminus, and the cell wall. This clone quantitatively releases the lipase hybrid protein in the culture supernatant in an active conformation.

The present invention relates to a method for identifying a nucleic acid which codes for a polypeptide factor affecting the covalent bonding of polypeptides to the surface of Gram-positive bacteria, comprising the following steps:

a) providing a sample of Gram-positive bacteria which can be genetically altered and contain or produce at least one enzymatic reporter substance which is or can become covalently bonded to the surface of the Gram-positive bacteria, said at least one reporter substance having a different enzymatic activity when not covalently bonded to the surface of the Gram-positive bacteria from that exhibited when it is covalently bonded to the surface of the Gram-positive bacteria;

b) causing genetic alterations in Gram-positive bacteria of the sample;

c) assaying the enzymatic activity of the reporter substance of the Gram-positive bacteria of the sample;

d) separating Gram-positive bacteria which exhibit a different enzymatic activity of the reporter substance from that observed for covalent bonding of the reporter substance to the surface of the Gram-positive bacteria;

e) isolating the nucleic acid of the Gram-positive bacteria separated in step d);

f) identifying at least one segment of the nucleic acid isolated in step e) that carries the genetic alteration;

g) based on the segment identified in step f), identifying a nucleic acid which codes for a polypeptide factor affecting the covalent bonding of polypeptides to the surface of Gram-positive bacteria.

Within the meaning of the method according to the invention, "when not covalently bonded" includes both non-covalent bonding to the surface of the Gram-positive bacteria and complete release.

Said assaying of the enzymatic activity of said at least one reporter substance of the Gram-positive bacteria of the sample can preferably be done by comparison with at least one reference sample which has not been genetically altered, and/or at least one reference sample in which the reporter substance is non-covalently bonded to the surface of Gram-positive bacteria, and/or at least one reference sample in which the reporter substance is covalently bonded to the surface of the Gram-positive bacteria, and/or at least one reference sample in which the reporter substance is present without covalent bonding to the surface of the Gram-positive bacteria.

It may be preferred to recover the nucleic acid identified according to step g) of the method. The polypeptides encoded in this nucleic acid can be used, in particular, in the screening for active substances.

As has been described above, said covalent bonding of the polypeptides is preferably bonding to the cell wall murein, especially to interpeptide bridges, such as pentaglycines of the cell wall of Gram-positive bacteria. The polypeptides are, in particular, pathogenicity factors of the Gram-positive bacteria.

The method according to the invention advantageously allows the selective identification of a nucleic acid which codes for a polypeptide factor which directly or indirectly affects the covalent bonding of polypeptides to the surface of Gram-positive bacteria. As set forth above, the putative process of surface anchoring comprises two specific steps:

a) cleavage between threonine and glycine of the LPXTG motif; and b) covalent bonding of the threonine to peptide components of the cell wall, especially the interpeptide bridge.

Thus, the method according to the invention detects those nucleic acids, in particular, which code for polypeptide factors which perform the cleavage reaction;

perform covalent bonding of the polypeptides;

are important to the integrity and the correct building of the cell wall.

In a preferred embodiment of the method according to the invention, a hybrid polypeptide having the following sequence segments, in particular, is used as a reporter substance: N-terminal signal peptide, enzyme, sequence segment having the sequence LPXTG, hydrophobic sequence segment, and charged sequence segment. As shown in the following Examples, *S. hyicus* lipase, in particular, can be used as the enzymatic component of the hybrid polypeptide. However, it may also be of advantage to use *E. coli* β-lactamase or other enzymes. Naturally occurring surface polypeptides as well as genetically engineered hybrid polypeptides may serve as reporter substances which can be detected in the medium due to the action of suitable genetic alterations in the bacteria to be examined, using the whole range of known chemical, biochemical and immunological methods. However, in order to ensure a high sample throughput while maintaining the reliability of the method according to the invention, it is advantageous, in particular, to use hybrid polypeptides having enzymatic activity as reporter substances.

In addition, it may be preferred to use reporter substances having at least one detectable property wherein said reporter substance has an altered detectable property when not covalently bonded to the surface of the Gram-positive bacteria as compared to that exhibited when it is covalently bonded to the surface of the Gram-positive bacteria.

It may further be preferred to provide the enzyme as a proenzyme.

In addition, it may be particularly preferred to determine the change in enzymatic activity due to a transition of the enzyme from an inactive to an active conformation or vice versa. This may preferably be achieved by using a linker peptide provided between the enzyme and the LPXTG motif.

In a preferred embodiment of the method according to the invention, the number of amino acids of the linker peptide is chosen such that the enzyme is anchored to the surface of the Gram-positive bacteria in an inactive conformation. When *S. hyicus* lipase is used, the number of amino acids in the linker peptide should be less than ten, in particular. In another embodiment, the enzyme could be directly fused with its C terminus to the LPXTG motif, avoiding the linker peptide. Thus, the Gram-positive bacteria bear inactive enzymes covalently bonded to their surface which, when not covalently bonded, especially if released from the surface of the Gram-positive bacteria, fold into an active conformation and thus undergo a detectable change in their enzymatic activity.

It is particularly preferred to perform the method according to the invention with those Gram-positive bacteria which have a low natural cell wall turnover and/or a small number of cell wall proteases and/or a small number of secreted proteases, in order to minimize the fraction of false positive results. Thus, the method according to the invention can be performed not only with naturally occurring Gram-positive bacteria, such as *S. carnosus,* but also with bacteria which are already genetically altered.

In addition, it may also be preferred to perform the method according to the invention with Lif expressing cells. Lysostaphin immunity factor (Lif) expressing Gram-positive cells exhibit modifications in the murein framework of the cell wall. These changes have no influence on the bonding reaction of cellular surface proteins in the cell wall. Example 2 describes a preferred embodiment of the method according to the invention for examining the anchoring of proteins in the cell wall of Lif expressing cells using the exemplary *S. hyicus* lipase or proLipFnBPB. The comparison of the enzymatic activity of the lipase on the cell wall and in the supernatant of the culture medium showed that the Lif expression has no influence on the secretion of the lipase or the anchoring of proLipFnBPB in the cellular surface.

In a particularly preferred embodiment of the method according to the invention, the assaying of the enzymatic activity of the reporter substance is done using fluorescence spectroscopy, especially confocal fluorescence spectroscopy, as shown in Example 1. In this case, it is possible to employ the known methods of one- or more-photon excitation. The method of fluorescence correlation spectroscopy (FCS), in particular, as described in detail in WO 94/16313, has proven an advantageous assaying method. Instead of the device described in the above mentioned patent application, it may also be preferred to perform FCS using elements of near-field spectroscopy as set forth in DE-C-44 38 391 and WO 96/13744. The mentioned documents are incorporated herein by reference.

WO 98/16814, which is incorporated herein by reference, describes a method for the analysis of samples containing particles by repeatedly measuring the number of photons per defined time interval of emitted light or light scattered in the sample, followed by a determination of the distribution function of the number of photons per defined time interval from which the distribution function of particle brightness is then determined. This method can also be preferably employed for the examination of luminescent, especially fluorescent, samples, a specific embodiment in which it is called fluorescence intensity distribution analysis (FIDA). The disclosure of these applications is incorporated herein by reference.

Dyes suitable for fluorescence measurements are known to those skilled in the art from the literature. For example, it may be preferred to determine the conversion of a substrate which undergoes a change in its fluorescence properties. Further, it may be preferred to employ a reporter assay using fluorescent or luminogenic proteins, such as GFP (green fluorescent protein).

In a preferred embodiment, the genetic alteration according to step b) of the method according to the invention is effected by transposon mutagenesis. However, UV mutagenesis or chemical mutagenesis, for example, may also be performed instead. Such methods are described in numerous publications and standard textbooks which are incorporated herein by reference (Miller J. H. (Ed.): Experiments in Molecular Genetics, Cold Spring Harbor, N.Y. 11724, Cold Spring Harbor Laboratory, 1977; Sambrook J., Fritsch E. F., and Maniatis T. (Eds.): Molecular Cloning, A Laboratory Manual; New York, Cold Spring Harbor Laboratory, 1989).

The exemplary organism S. carnosus, which is non-pathogenic, exhibits a markedly low release of cell wall subunits and does not produce any interfering exo-proteases. Its relationship to the pathogenic staphylococci, such as S. aureus, S. hyicus or S. epidermidis, enables transfer of the results achieved here in an exemplary manner to organisms which are medicinally more relevant.

Thus, for example, it is possible to perform the method according to the invention in the non-pathogenic organism S. carnosus as far as steps a) to f) are concerned. The segment identified according to step f) can then serve as a basis for identifying, not only in the wild type strain, but also in related strains, those nucleic acids which code for a polypeptide factor affecting the covalent bonding of polypeptides to the surface of these strains. This may be done in a manner known to those skilled in the art, such as hybridization with gene probes or PCR amplification of the corresponding genes.

Another embodiment of the method according to the invention detects the anchoring of the reporter substances at the cellular surface, in addition to assaying their enzymatic activity. This further embodiment of the method according to the invention as described in Example 4 allows to establish whether proteins are prevented from being released by non-covalent bonds. This special embodiment allows to determine in which way the reporter substance is bound to the murein framework. According to FIG. 3, muramidase Ch preferably cuts into the cell wall of Gram-positive bacteria so that proteins anchored in the cell wall are cleaved together with cell wall fragments of variable length (Schneewind et al., EMBO J. 12: 4803–4811, 1993). In contrast, non-covalently bonded proteins cleaved by muramidase Ch all have the same molecular weight (Schneewind et al., EMBO J. 12: 4803–4811, 1993). According to this particular embodiment, the distinction between the different cleavage products is done by SDS-PAGE (sodium dodecylsulfate polyacrylamide gel electrophoresis) and immunoblotting. For illustrative purposes, the SDS-PAGE running behavior of covalently anchored proteins after release by muramidase Ch and lysostaphin treatment is shown in FIG. 4.

In a particularly preferred embodiment of the method according to the invention, distinction can be made in the culture medium as to whether the release of cell wall proteins was caused by the action of genetic alterations which affect the anchoring mechanism at the surface of Gram-positive bacteria or by natural changes of the cell wall. In addition to the assaying of the enzymatic activity according to the invention, characterization of the released polypeptides is performed. Example 5 illustrates this with proLipFnBPB from pTX30 and pTX30/pCXlif-expressing cells. ProLipFnBPB released from these cells by natural changes of the cell wall shows unresolved or poorly resolved (expanded) bands of lipases of different lengths in the gel-electrophoretic examination and subsequent immunoblotting. Instead of an expanded band consisting of a number of overlapping lipase-specific signals, cell wall proteins directly released from the cell, as the proteins obtained by the action of lysostaphin (80 mg·ml$^{-1}$ in BM, 30 min at 37° C.) from the supernatant of non-Lif-expressing cells, show a narrow, sharply bounded band in SDS-PAGE and subsequent immunoblotting.

The present invention also relates to the nucleic acids identified, and preferably isolated, by the method according to the invention.

The stated specific nucleic acid sequences were obtained by sequencing the regions of S. carnosus genomic DNA adjacent to the insertion sites of the transposon.

EXAMPLE 1

Simulation Scenarios

Strains and Plasmids

The wild type strain S. carnosus TM300 (Götz, F., J. Appl. Bacteriol. Symp. Supp. 69: 49–53, 1990) was used as the host organism for the production of all recombinant Staphylococcus strains. The preparation of the assay plasmid pTX30Δ82 is described below in Example 2.

The plasmids pTX30Δ82.mem and pTX30Δ82.sec were prepared by analogy with the plasmid pTX30Δ82 using the oligonucleotide pairs (SEQ. ID. NOS. 12 to 15) AS14 (5'-ATAAGGCGCCTTAGTTTAATTATGCTTTGTG ATTC)/AS45 (5'-CGCAGGAAGCTTACCACAAT CTAAGAAATCTGAAATATCTCAAGCAAGTGGAG AAG)and AS42 (5'-AATAAGGCGCCTCATTATCCACCTGTTTCA GGTAGTTC)/ AS22 (5'-ACGAAAGCTTA CCACAATCTAAGAAATCTGAAC), starting with pTX30. The plasmids pTX30Δ82, pTX30Δ82.mem and pTX30Δ82.sec were transformed into S. carnosus TM300 (Götz and Schumacher, FEMS Microbiol. Lett. 40: 285–288, 1987).

Media

For culturing the bacteria in liquid culture, basal medium (BM) was used which contained 1% peptone, 0.5% yeast extract, 0.5% NaCl, 0.1% glucose and 0.1% dipotassium hydrogenphosphate (pH 7.4). For the induction of the xylose promoter, modified basal medium (induction medium) was used in which the glucose had been replaced by 0.5% xylose. According to need, chloramphenicol (Cm, 10 mg/l), tetracyclin (Tc, 25 mg/l) and erythromycin (Em, 2.5 mg/l) was added to the BM. Agar selection plates were supplemented with 15 g/l agar. Lipase test plates were prepared using tributyrin-agar base (Merck) according to the supplier's instructions. Prior to casting the plates, 1% glycerol tributyrate and the corresponding antibiotics (Tc, Em) were added to the agar. On these plates, lipase-releasing bacterial cells can be identified by the formation of clear halos.

Figure 2:
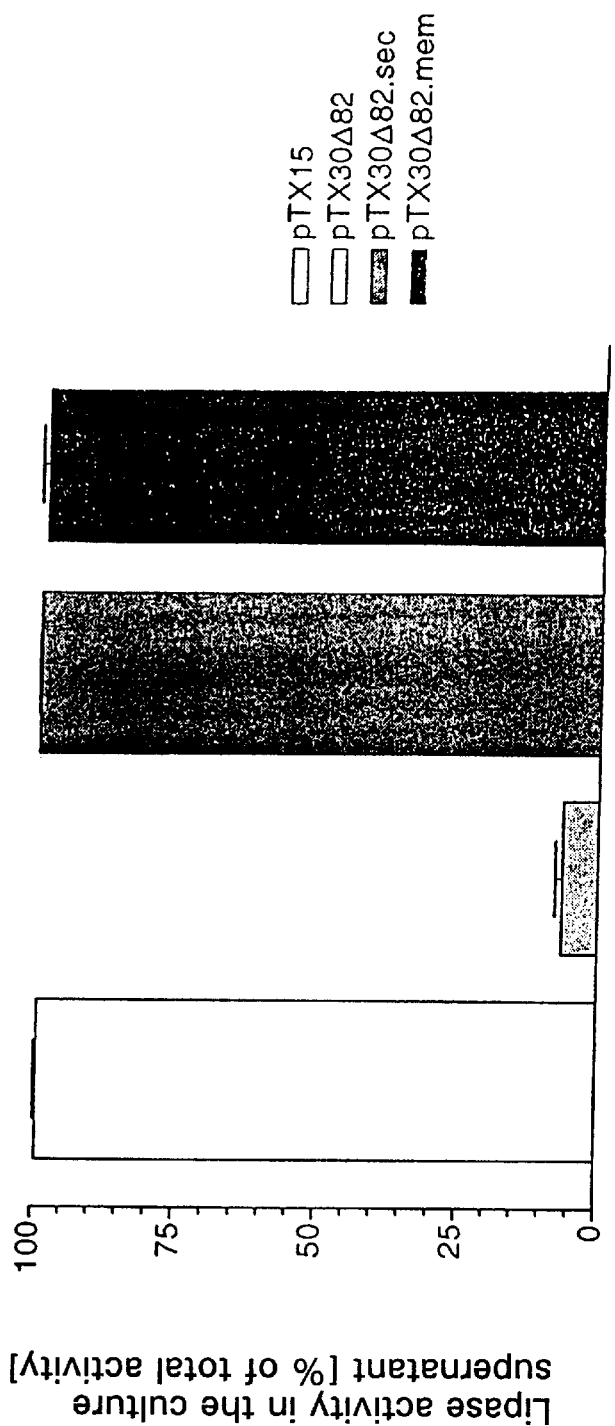
FIG. 2 shows the quantification of the lipase activity in the simulations clones. The respective lipase activity in the culture supernatant was determined in relation to the total activity of the respective clone.

Part I: Localization and Quantification of Lipase Activity in the Simulation Clones 5 ml each of basal medium were inoculated from a plate with the wild type strain S. carnosus TM300 or the above described S. carnosus clones and incubated at 37° C. over night with shaking. With these procultures, 5 ml each of induction medium was inoculated at 1:100 and shaken at 37° C. until the late logarithmic growth stage was reached. The cultures were cooled to 4° C. prior to determining the lipase activity in the culture supernatant and the cell-bound lipase activity after release by treating the cells with lysostaphin according to Strauβ and Götz (Mol. Microbiol. 21: 491–500, 1996). The total activity was obtained as the sum of the cell-bound activity and the activity in the culture supernatant. Subsequently, the respective lipase activity in the culture supernatant was determined in relation to the total activity of the corresponding clone (FIG. 2).

Part II: Establishing of a Fluorescence-spectroscopy Based Assay Method

The S. carnosus clones S. carnosus/pTX30Δ82, /pTX30Δ82.mem and /pTX30Δ82.sec were cultured over night at 37° C. in basal medium. The cell densities of these cultures were determined by measuring the optical densities (OD576) in a photometer, and dilutions (about 1:200) of equal cell densities were prepared. For preparing these dilutions, modified basal medium (induction medium) was used. Then, the diluted cultures were again allowed to grow at 37° C. In various experiments, both microtitration plates and other vessels were used for the cultures.

At different times of cultivation, the lipase activity released by the bacteria was determined in the culture supernatants. The cells were pelletized by centrifugation, the culture supernatants were taken off and, if necessary, stored on ice. Assays were performed in microtitration plates (100 μl) with glass bottoms. The lipase assay buffer was constituted as follows: 10 mM $CaCl_2$, 0.05% Triton X-100, 20 mM Tris/HCl, pH 8.0. As the fluorogenic dye substrate, 1,2-o-dilauryl-rac-glycero-3-glutaric acid resorufin ester (Sigma # D7414) was used. The substrate stock solution was prepared in 100% DMSO at 1 mg/ml and stored at −20° C. Per measuring sample, 10 μl each of the culture supernatants was mixed with 80 μl lipase assay buffer and 10 μl substrate solution (10 μM final concentration). The conversion of the substrate was determined by fluorometry using a fluorescence (ELISA) reader, or by means of a fluorescence correlation spectrometer (e.g., ConfoCor™, Carl Zeiss Jena GmbH and Evotec, Germany).

While clone S. carnosus/pTX30Δ82 gave insignificantly higher signals than those from the negative control (only buffer and substrate) in the measurements, significant amounts of lipase activity were found in the culture supernatants of the two clones S. carnosus/pTX30Δ82.mem and S. carnosus/pTX30Δ82.sec.

EXAMPLE 2

Figure 1:
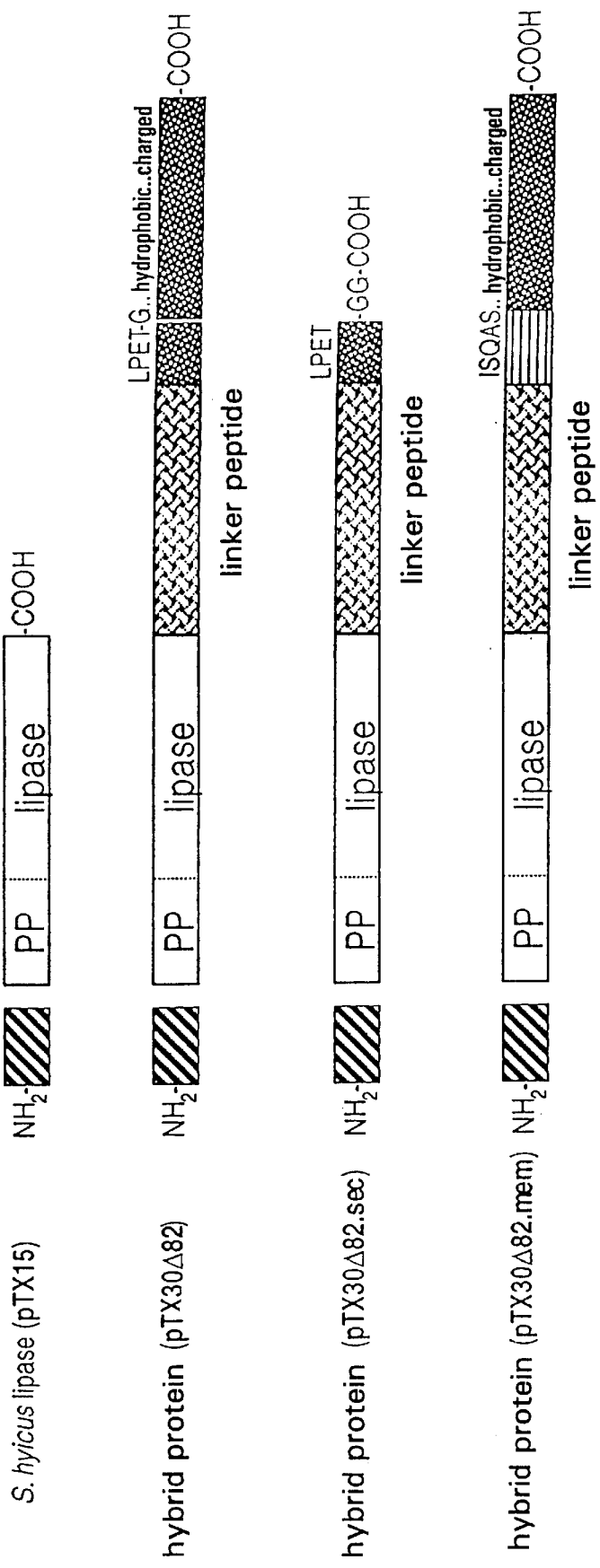
FIG. 1 illustratively describes the structure of a hybrid protein which can be employed as a reporter substance (assay plasmid pTX30Δ82) and the above mentioned structures of the hybrid proteins used for the simulation of the method according to the invention (plasmids pTX30Δ82.sec and pTX30Δ82.mem) in comparison to the structure of S. hyicus lipase (plasmid pTX15). At the N terminus, there is located the so-called signal peptide (cross-hatched) which enables the transport of the proenzyme (schematically represented by PP and lipase) through the cytoplasmic membrane and is removed proteolytically in the course of the secretory processing. The lipase is preferably followed by a linker peptide whose length is selected in such a way that the lipase can be anchored at the surface of the Gram-positive bacteria in an inactive conformation. This is followed by the LPETG motif, hydrophobic and charged sequence segments (assay plasmid pTX30Δ82). In the hybrid protein used for the simulation (plasmid pTX30Δ82.mem), the LPXTG motif is replaced by the sequence ISQAS. In the hybrid protein used for another simulation (plasmid pTX30Δ82.sec), the linker peptide is followed only by a sequence segment of the sequence LPETGG.

Screening of Mutants for Defects in Surface Anchoring Due to Transposon Mutagenesis Strains and Plasmids Wild type strain *S. carnosus* TM300 (Götz, F., J. Appl. Bacteriol. Symp. Supp. 69: 49–53, 1990) was transformed with the assay plasmid pTX30Δ82 as described by Götz and Schumacher (FEMS Microbiol. Lett. 40: 285–288, 1987). Plasmid pTX30Δ82 was prepared by analogy with the plasmid pCX30Δ82 (Strauβ and Götz, Mol. Microbiol. 21: 491–500, 1996). However, rather than the chloramphenicol selectable plasmid pCX15 (Wieland et al., Gene 158: 91–96, 1995), the tetracyclin selectable plasmid pTX15 (Peschel et al., FEMS Microbiol. Lett. 137: 279–284, 1996) was used as the starting vector. This plasmid contains a gene fusion which encodes the assay hybrid protein (proLipFnBPBAΔ82) consisting of *S. hyicus* lipase and the C-terminal portion of the fibronectin binding protein B (FnBPB) and which is under the control of the inducible xylose promoter (Wieland et al., Gene 158: 91–96, 1995). The distance between the C-terminal alanine residue of the lipase and the leucine residue of the LPXTG motif of FnBPB was 10 amino acids (FIG. 1). For the transposon mutagenesis, this strain was additionally transformed with the plasmid pTV1ts (Youngman et al. in: Smith et al. (Eds.): Regulation of procaryotic development. American Society for Microbiology, Washington D.C., 65–87, 1989).

The sequences of the nucleic acids used herein have been deposited in gene banks: gene bank entry number: plasmid pT181: g151679; xylR (*S. xylosus*): g48833; lip (*S. hyicus*): g488333; plasmid pC194: g150548; fnbB (*S. aureus*): g49040.

The references cited are incorporated herein by reference.

Media

The media used corresponded to those stated in Example 1.

Transposon Mutagenesis

Plasmid pTV1ts, which exhibits temperature-sensitive replication in Gram-positive bacteria, codes for chloramphenicol resistance and carries the transposon Tn917 which includes an erythromycin resistance gene (Youngman et al. in: Smith et al. (Eds.): Regulation of procaryotic development. American Society for Microbiology, Washington D.C., 65–87, 1989). *S. carnosus* cells carrying the plasmids pTV1ts and pTX30Δ82 were grown over night in BM selection medium (Cm, Tc, Em) at 30° C. BM selection medium (Tc, Em) 1:100 was inoculated with this proculture, and the Tn917 was mobilized at the non-permissive temperature of 40° C. for at least 20 cell generations.

Screening of Mutants for Defects in Surface Anchoring

Mutants having a transposon mobilization rate (the cells being Tc+Em resistant, but Cm sensitive) of at least 1000:1 were directly plated on lipase test plates and incubated at 30° C. for about 48 h before potential mutants having defects in covalent cell wall anchoring were identified. These were characterized by a clear halo produced by the released lipase activity. On agar selection plates (Tc, Em), the relevant clones were again separated into isolated cells before their phenotypes were again verified on lipase test plates and in liquid culture. Thus, 5 ml each of induction medium was inoculated from a plate and shaken at 30° C. over night before the lipase activity in the culture supernatant was determined in comparison to the non-mutated starting strain, as described by Strauβ and Götz (Mol. Microbiol. 21: 491–500, 1996).

EXAMPLE 3

Strains and Plasmids

The wild type strain *S. carnosus* TM300 (Götz, F., J. Appl. Bacteriol. Symp. Supp. 69: 49–53, 1990) was used as the host organism for the production of all recombinant Staphylococcus strains. The plasmids pTX15, pTX30 (encodes ProLipFnBPB, a hybrid protein consisting of *S. hyicus* lipase linked to the C terminus of *S. aureus* fibronectin binding protein B) and pCXlif (lif, lysostaphin immunity factor) were transformed into *S. carnosus* TM300 as described by Götz and Schumacher (FEMS Microbiol. Lett. 40: 285–288, 1987).

The construction of pCXlif was effected according to the method described by Thumm and Götz (Mol. Microbiol. 23: 1251–1256, 1997).

The plasmid pTX30 was prepared by insertion of the BamHI-NarI fragment of pCX30 (Strauβ and Götz, Mol. Microbiol. 21: 491–500, 1996) into the plasmid pTX15 cut with the same restriction enzymes.

The genes were expressed under the control of the xylose promoter system (Wieland et al., Gene 158: 91–96, 1995). The induction of the expression was effected as described by Strauβ and Götz (Mol. Microbiol. 21: 491–500, 1996).

The references mentioned are incorporated herein by reference.

Media

The bacteria were cultured in basal medium (BM; see Example 1) at 30° C. According to need, chloramphenicol (Cm, 10 mg/l) or tetracyclin (Tc, 25 mg/l) was added to the basal medium.

The influence of the lysostaphin immunity factor (Lif) on the secretion and anchoring of *S. hyicus* lipase or proLipFnBPB in the cell wall by comparing the lipase activities on the cell wall and in the supernatant of the culture medium.

The cell cultures (pTX15, pTX30, pTX15+pCXlif, pTX30+pCXlif) were first separated into cell pellets and medium by centrifugation. Then, the pellets were washed three times with BM and taken up in BM. Cell wall proteins released from pTX30 expressing cells by treatment with lysostaphin (80 μg/ml in BM; 30 min at 37° C.) served as the reference. Dilutions from the samples were made. Thus, 95 μl of lipase assay buffer (10 mM $CaCl_2$, 0.1% Triton X-100 and 20 mM Tris-HCl, pH 8.5) containing the chromogenic lipase substrate p-nitrophenyl caprylate [Sigma] in a concentration of 5 mM was added to 5 μl each of the culture supernatants. The hydrolysis of the substrate was subsequently followed over 10 minutes at 30° C. photometrically using a microtitration plate (ELISA) reader (SpectraMax, Molecular Devices) or by means of fluorescence correlation spectroscopy with ConfoCor at a wavelength of 405 nm. The assays were performed in microtitration plates with or without a glass bottom.

All in all, it was found that the total lipase activity in the supernatant was 99.2% for cells expressing pXT15, and 99.1% in cells expressing both pXT15 and pCXlif. In comparison, cells containing pTX30 have 85.1% of their lipase activity at the cellular surface, just like cells which express both pTX30 and pCXlif (84.5%).

Thus, it could be shown that Lif expression has no influence on the secretion of lipase or the anchoring of proLipFnBPB in the cellular surface.

EXAMPLE 4

Strains and Plasmids

The strains and plasmids used are those mentioned in Example 2.

Media

The bacteria were cultured in basal medium (BM; see Example 1) at 30° C. According to need, chloramphenicol (Cm, 10 mg/l) or tetracyclin (Tc, 25 mg/l) was added to the basal medium.

Determination of the Enzymatic Activity of the Released Proteins

The lipase activity released by the bacteria was determined in the culture supernatants as follows:

The cells were sedimented by centrifugation, the culture supernatants were taken off and, if necessary, stored on ice. Assays were performed in microtitration plates without a glass bottom. The lipase assay buffer (10 mM $CaCl_2$, 0.1% Triton X-100 and 20 mM Tris/HCl, pH 8.5) contained the chromogenic lipase substrate p-nitrophenyl caprylate [Sigma] in a concentration of 5 mM. Per measuring sample, 5 µl each of the culture supernatants was mixed with 95 µl lipase assay buffer. The conversion of the substrate was determined by photometry using a microtitration plate (ELISA) reader.

Figure 3:
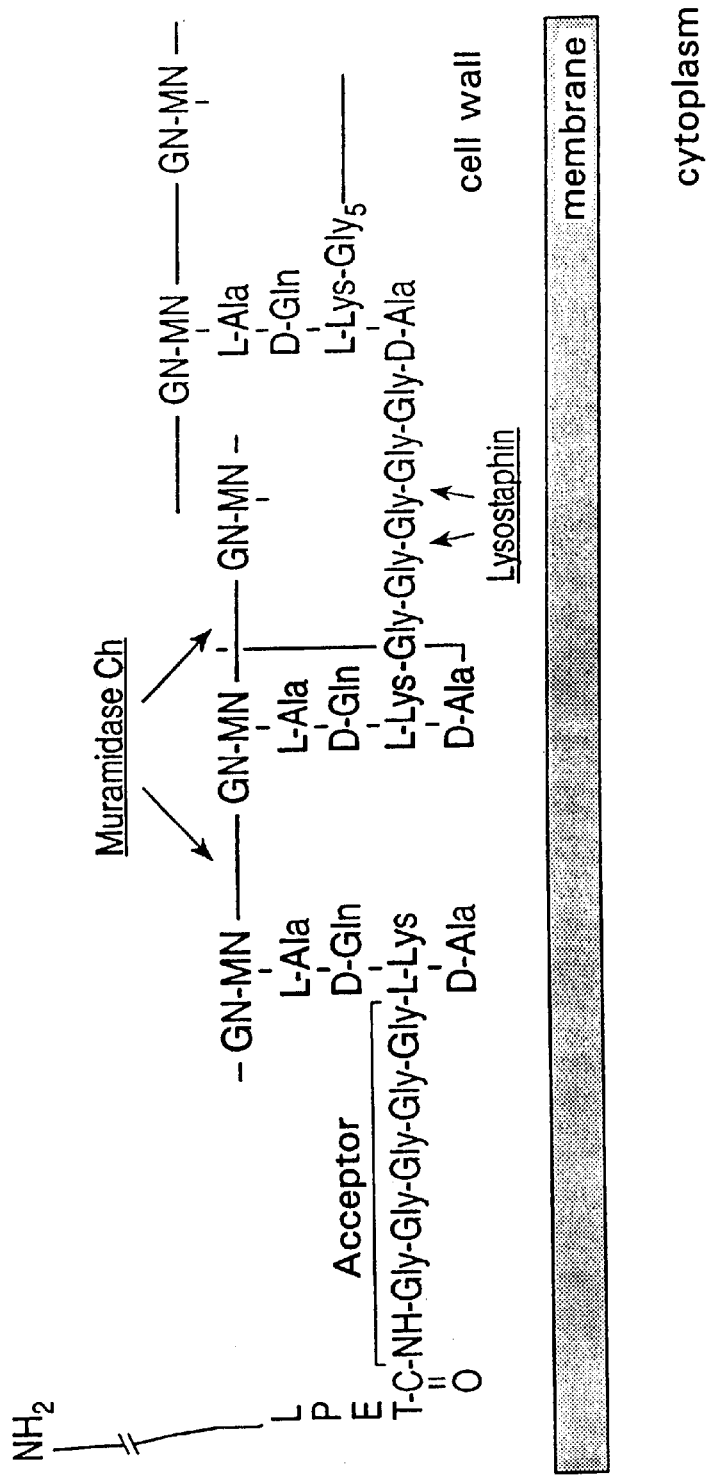
FIG. 3 shows the structure of the peptidoglycane in Staphylococci with a C-terminally linked surface protein. The cleavage sites for muramidase Ch and lysostaphin are highlighted.

Distinction Between Proteins which are Covalently or Non-covalently Bonded to the Cell Wall In order to exclude that any proLipFnBPB is non-covalently bonded to the cell wall of the expressing cells and for this reason is not covered in the determination of the enzymatic activity in the supernatant, a strategy has been developed which is based on the use of muramidase Ch and lysostaphin. Muramidase Ch hydrolyzes the β-1,4-linkage of N-acetylmuramic acid and acetylglucosamine (FIG. 3) (Ghuysen, Bacteriol. Rev. 32: 425–464, 1968). It does not cut directly at the linkage sites of the surface proteins to the cell wall so that the proteins are cleaved together with cell wall fragments of variable lengths (Schneewind et al., EMBO J. 12: 4803–4811, 1993). In contrast, non-covalently bonded proteins cleaved by muramidase Ch all have the same molecular weight (Schneewind et al., EMBO J. 12: 4803–4811, 1993).

The mentioned references are incorporated herein by reference.

The cells were obtained from 500 µl culture medium by centrifugation. Then, the pellets were washed three times with water and precipitated by adding trichloroacetic acid (7% w/v) (20 min on ice). After centrifuging the precipitate, the pellet formed was washed twice with acetone and dried in vacuo. The pellets were then dissolved in 170 µl BM to which muramidase Ch (100 µg·ml$^{-1}$) had been added, and the solution was incubated at 37° C. for 3 h. Then, the samples were again centrifuged, and the supernatant was divided into two aliquots of 80 µl each; 20 µl of water was added to one of them, and 20 µl of lysostaphin solution (400 mg·ml$^{-1}$) was added to the other. The solutions were incubated at 37° C. for 30 min. The individual aliquots were then concentrated and examined using SDS-PAGE (10% acrylamide) and immunoblotting (with prolipase-specific antiserum).

It was found (FIG. 4) that muramidase Ch results in complete release of proripFnBPB from the cell wall of S. carnosus, irrespective of whether or not Lif (pCXlif) was also expressed in these cells. In both cases, a spectrum of lipase-specific signals could be seen on the gel as an expanded band which is due to cell wall fragments of different lengths covalently bonded to proLipFnBPB.

Figure 4:
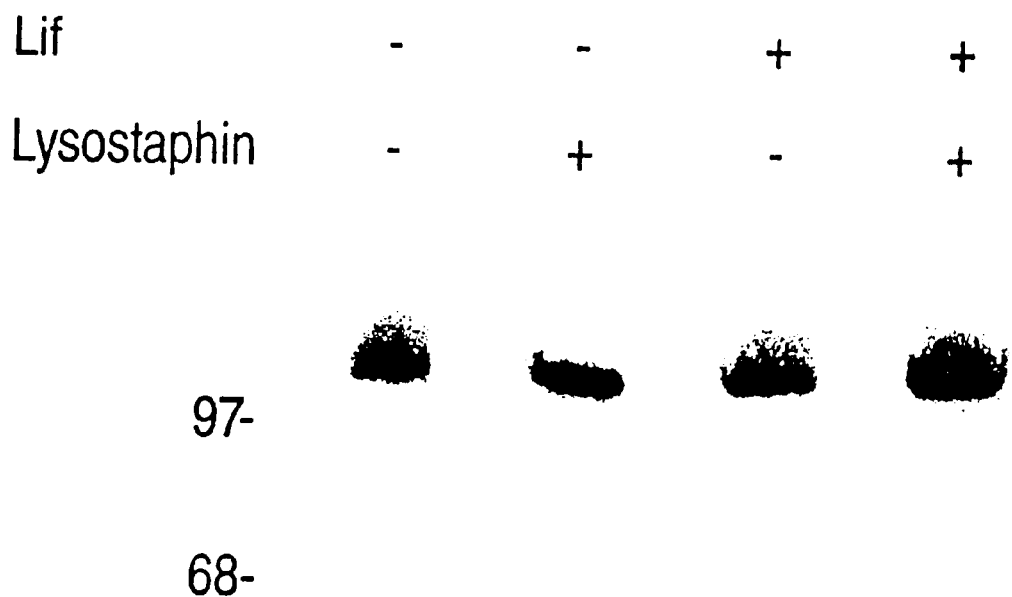
FIG. 4 represents the influence of lysostaphin on the cellular surface proteins which were released from the cell wall of S. carnosus by muramidase Ch. ProLipFnBPB was synthesized in these cells in the presence (+) or absence (−) of Lif (pCXLif). The released hybrid proteins were incubated in the presence (+) or absence (−) of lysostaphin and subsequently characterized by SDS-PAGE (10% acrylamide) and immunoblotting (prolipase-specific antiserum) according to Strauβ and Götz (Mol. Microbiol. 21: 491–500, 1996). The molecular weights of the protein standards(in kDa) are given on the left margin.
Figure 5:
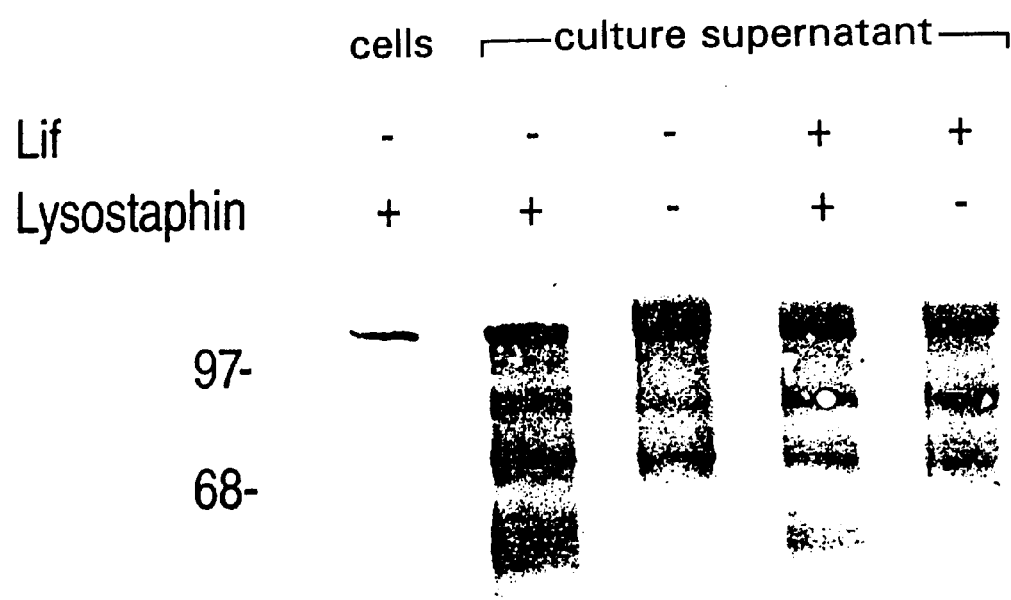
FIG. 5 shows the influence of lysostaphin on proLipFnBPB which was released from S. carnosus into the culture medium by natural cell wall changes. Supernatants of cells expressing proLipFnBPB (pTX30) in the presence (+) or absence (−) of Lif (pCXLif) were examined in the presence (+) or absence (−) of lysostaphin. As the reference, there was used proLipFnBPB released by the action of lysostaphin from the cell wall of S. carnosus cells which only contained the plasmid pTX30. The proteins were separated by SDS-PAGE (10% acrylamide), and immunoblotting (prolipase-specific antiserum) was performed. The molecular weights of the standard molecules are given on the left margin.

For the discrimination of Lif-expressing cells, the samples were treated with lysostaphin in a parallel run prior to performing the gel electrophoresis and the immunoblotting. It was found that in the cases in which proLipFnBPB was released from cells which did not express Lif, the residues of the cell wall anchoring were completely removed. On the gel, this could be seen as a sharp band. Surface proteins derived from Lif-expressing cells were not lysostaphin-sensitive (FIG. 4).

EXAMPLE 5

Strains and Plasmids

The strains and plasmids used are those mentioned in Example 2.

Media

The bacteria were cultured in basal medium (BM; see Example 1) at 30° C. According to need, chloramphenicol (Cm, 10 mg/l) or tetracyclin (Tc, 25 mg/l) was added to the basal medium.

Determination of the Enzymatic Activity of the Released Proteins

The lipase activity released by the bacteria was determined in the culture supernatants in accordance with Example 3.

Determination of the Fraction of Surface Proteins Released from S. Carnosus by Natural Cell Wall Changes One important characteristic of cell wall proteins released by natural cell wall changes is being covalently bonded to the cell wall prior to the release.

For determining the fraction of naturally released proteins, the culture supernatant of cells containing the plasmids pCXLif and/or pTX30 was concentrated and analyzed by SDS-PAGE and immunoblotting. proLipFnBPB released by lysostaphin from cells which only contained the plasmid pTX30 was used as the reference. In addition to decomposition products which had a greater electrophoretic mobility than that of the reference, a number of overlapping lipase-specific signals were observed as an expanded band. Incubation of the supernatant with lysostaphin (80 mg·ml$^{-1}$ in BM, 30 min at 37° C.) prior to gel electrophoresis and immunoblotting had an effect only on those proteins which had been obtained from the supernatant of non-Lif-expressing cells. Instead of the expanded band from a number of over-lapping lipase-specific signals, a limited band can be seen which exhibits the same electrophoretic mobility as the reference. The lipase-specific signals derived from cells which express Lif and proLipFnBPB are not affected by lysostaphin.

In this study, it was found, in addition, that a total of 5% of the total lipase activity of cells expressing ProLipFnBPB by low-copy number plasmids, was measured in the supernatant from natural release whereas even 15% of the total lipase activity could be determined in the supernatant for medium-copy number plasmids. The coexpression of other surface proteins had no influence on the release of lipase.

What is claimed is:

1. A method for identifying a nucleic acid which codes for a polypeptide factor affecting the covalent bonding of polypeptides to the surface of Gram-positive bacteria, comprising the following steps:
   a) providing a sample of Gram-positive bacteria which can be genetically altered and contain or produce at least one enzymatic reporter substance which is or can become covalently bonded to the surface of the Gram-positive bacteria, said at least one reporter substance having a different enzymatic activity when not covalently bond ed to the surface of the Gram-positive bacteria from that exhibited when it is covalently bonded to the surface of the Gram-positive bacteria;
   b) causing genetic alterations in Gram-positive bacteria of the sample;
   c) assaying the enzymatic activity of the reporter substance of the Gram-positive bacteria of the sample;
   d) separating Gram-positive bacteria which exhibit a different enzymatic activity of the reporter substance from that observed for covalent bonding of the reporter substance to the surface of the Gram-positive bacteria;
   e) isolating the nucleic acid of the Gram-positive bacteria separated in step d);
   f) identifying at least one segment of the nucleic acid isolated in step e) that carries the genetic alteration;
   g) based on the segment identified in step f), identifying a nucleic acid which codes for a polypeptide factor affecting the covalent bonding of polypeptides to the surface of Gram-positive bacteria.

2. The method according to claim 1, characterized in that the enzymatic activity of the reporter substance is determined in comparison to at least one reference sample which has not been genetically altered, and/or at least one reference sample in which the reporter substance is non-covalently bonded to the surface of Gram-positive bacteria, and/or at least one reference sample in which the reporter substance is covalently bonded to the surface of the Gram-positive bacteria, and/or at least one reference sample in which the reporter substance has no covalent bonding to the surface of the Gram-positive bacteria.

3. The method according to claims 1, characterized in that the nucleic acid identified according to step g) is recovered.

4. The method according to claim 1, characterized in that said polypeptides are pathogenicity factors of Gram-positive bacteria.

5. The method according to claim 1, characterized in that said reporter substance is a hybrid polypeptide.

6. The method according to claim 5, characterized in that said hybrid polypeptide has a succession of the following sequence segments: N-terminal signal peptide, enzyme, sequence segment having the sequence LPXTG, hydrophobic sequence segment, and charged sequence segment.

7. The method according to claim 6, characterized in that said enzyme is provided as a proenzyme.

8. The method according to claim 1, characterized in that said Gram-positive bacteria have a low natural cell wall turnover and/or a small number of cell wall proteases and/or a small number of secreted proteases.

9. The method according to claim 1, characterized in that the fraction of reporter substances released by natural cell wall changes is determined.

10. The method according to claim 1, characterized in that the fraction of reporter substances which are non-covalently bonded to the surface of Gram-positive bacteria is determined.

11. The method according to claim 1, characterized in that said covalent bonding of the polypeptides is effected to the murein of the cell wall of Gram-positive bacteria.

12. The method according to claim 11, characterized in that said covalent bonding of the polypeptides is effected to the murein of the cell wall at interpeptide bridges.

13. The method according to claim 12, characterized in that the interpeptide bridges are pentaglycines.

14. The method according to claim 5, characterized in that the different enzymatic activity is due to a transition of the enzymatic reporter substance from an inactive to an active conformation or vice versa.

15. The method according to claim 5, characterized in that a linker peptide is provided between said enzyme and said sequence segment having the sequence LPXTG.

16. The method according to claim 15, characterized in that the linker peptide comprises less than 10 amino acids.

17. The method according to claim 1, characterized in that said assaying of the enzymatic activity of the reporter substance is done using fluorescence spectroscopy.

18. The method according to claim 17, characterized in that the fluorescence spectroscopy is confocal fluorescence spectroscopy.

19. The method according to claim 1, characterized in that said Gram-positive bacteria express lysostaphin immunity factor.

* * * * *